United States Patent [19]

Dolling et al.

[11] Patent Number: 5,093,498
[45] Date of Patent: Mar. 3, 1992

[54] TRIFLUOROMETHYLBENZYL CONTAINING QUATERNARY SALTS

[75] Inventors: Ulf H. Dolling, Westfield; Seemon H. Pines, Murray Hill; Edward J. J. Grabowski, Westfield, all of N.J.

[73] Assignee: Merck & Co., Inc., Rahway, N.J.

[21] Appl. No.: 724,415

[22] Filed: Jun. 28, 1991

Related U.S. Application Data

[60] Continuation of Ser. No. 547,537, Jun. 29, 1990, abandoned, which is a continuation of Ser. No. 366,261, Jun. 12, 1989, abandoned, which is a continuation of Ser. No. 246,908, Sep. 16, 1988, abandoned, which is a continuation of Ser. No. 60,947, Jun. 15, 1987, abandoned, which is a continuation of Ser. No. 752,324, Jul. 5, 1985, abandoned, which is a division of Ser. No. 579,341, Feb. 17, 1984, Pat. No. 4,578,509, which is a continuation-in-part of Ser. No. 481,200, Apr. 1, 1983, abandoned.

[51] Int. Cl.$^5$ .............................................. C07D 453/04
[52] U.S. Cl. ............................................................ 546/134
[58] Field of Search ........................................... 546/134

[56] References Cited

U.S. PATENT DOCUMENTS 2,111,227  3/1938  Salzberg .............................. 546/134

OTHER PUBLICATIONS

Colonna et al., J. C. S. Perkin I, pp. 547–552, (1981).
Colonna et al., J. C. S. Perkin I, pp. 371–373, (1978).
Julia et al., Tet. Letters, vol. 21, pp. 3709–3712, (1980).

*Primary Examiner*—Bernard Dentz
*Attorney, Agent, or Firm*—Richard S. Parr; Charles M. Caruso

[57] ABSTRACT

A process is disclosed for obtaining manipulated proportions of the (+) and (−) enantiomers of [(6,7-dichloro-2,3-dihydro-2-methyl-1-oxo-2-phenyl-1H-inden-5-yl)oxy]acetic acid by asymmetric chiral phase transfer catalysis.

1 Claim, No Drawings

TRIFLUOROMETHYLBENZYL CONTAINING QUATERNARY SALTS

This is a continuation of Ser. No. 07/547,537 filed June 29, 1990, now abandoned, which is a continuation of Ser. No. 07/366,261 filed June 12, 1989, now abandoned which is a continuation of Ser. No. 07/246,908 filed Sept. 16, 1988, now abandoned which is a continuation of Ser. No. 07/060,947 filed June 15, 1987, now abandoned, which is a continuation of Ser. No. 06/752,324 filed July 5, 1985, now abandoned which is a diversion of Ser. No. 06/579,341, filed Feb. 17, 1984, now U.S. Pat. No. 4,578,509 which is a continuation-in-part of Ser. No. 06/481,200, filed Apr. 1, 1983, now abandoned.

BACKGROUND OF THE INVENTION

1. Field of the invention

The present invention is directed toward balancing the uricosuric and diuretic properties of indacrinone, a racemic compound, through a process which enables the proportion of its (+) and (−) enantiomers to be manipulated.

There continues to be a great deal of interest in the discovery and development of diuretics which are also uricosuric, since many currently available diuretics commonly lead to urate retention, hyperuricemia, and, occasionally, attacks of gout. Hyperuricemia, in turn, may itself be a risk factor for the development of cardiovascular disease, carbohydrate intolerance, and urate-induced nephropathy. A large percentage of hypertensive patients also have hyperuricemia.

For example, ticrynafen, or tienilic acid, produces a prompt diuresis with an increased excretion of sodium and chloride, while at maximal drug effect, uric acid clearance increases about five-fold. Although this drug was approved for use as an antihypertensive agent in the U.S. in 1979, it was later withdrawn when unacceptably high incidences of hepatotoxicity were revealed.

Uric acid transport by the renal tubules involves both readsorptive and secretory processes. There has been an interest in the mechanism of action of drugs that directly influence tubular transport 29stems for uric acid and thus alter the rate of uric acid excretion. Probenecid, for example, increases the urinary excretion of uric acid by inhibition of carrier-mediated reabsorption. Likewise, indacrinone or indacrynic acid, which is the subject of the present invention, inhibits urate reabsorption in the proximal tubule.

The action of uricosuric agents is often seemingly contradictory, because of the complexity of the transport mechanisms involved. Thus, increase, decrease, or lack of effect on the excretion of uric acid is not only highly species dependent, but dosage dependent as well. Moreover, depending on the exact conditions, the combined effect of two uricosuric drugs may be either additive or antagonistic.

The renal transport of uric acid in mammals involves both secretion and reabsorption. However, in man the process of reabsorption dominates so that the amount that is excreted is but a small fraction of that which is filtered. A variety of factors, including uricosuric drugs, can influence the relative importance of these bidirectional transport mechanisms in man. As also indicated above, uric acid is transported by carrier-mediated mechanisms, not by diffusion and in man the site of transport is located in the proximal tubule, including both the convoluted and straight portions.

2. Brief Description of the Prior Art

It should be noted that in the biomedical literature, "indacrinone" is most frequently employed as a generic name, although it is also used to refer to the racemic mixture. As a racemic mixture, and as the (+) or (−) enantiomer, "indacrinone" is disclosed in U.S. Pat. No. 4,096,267 by its chemical name: [(6,7-dichlore-2,3-dihydro-2-methyl-1-oxo-2-phenyl-1H-inden-5-yl) oxy]acetic acid. This patent also refers generally to the possibility of combining different indanones disclosed where greater diuretic activity and greater uricosuric activity are possessed by said indanones. However, this patent does not suggest manipulation of the proportion of (+) and (−) enantiomers of indacrinone within critical limits, for careful balancing of uricosuric and diuretic properties to give maximum therapeutic benefit.

The different pharmacodynamic effects of the (+) and (−) enantiomers of indacrinone, specifically that the principal saluretic activity of indacrinone resides in the (−) enantiomer while uricosuric activity is present in both (−) and (+) enantiomers, are described by Irvin et al., *Clin. Pharmacol. Ther.*, p. 260 (Feb. 1980); deSolms et al., *J. Med. Chem.*, Vol. 21, No. 5, pp. 437–443 (1978); and Woltersdorf et al. *ACS Symposium Series No. 83 Diuretic Agents*, pp. 219–220 (1978). These publications also do not suggest manipulation of the proportion of (+) and (−) enantiomers of indacrinone within critical limits so as to achieve the maximum therapeutic benefit from balanced uricosuric and diuretic properties, as is the case with the present invention.

British Pat. No. 1,475,177 discloses the combination of indacrinone racemic mixture or the (−) enantiomer of indacrinone with a potassium-sparing pyrazinoyl-guanidine diuretic, especially amiloride. However, this patent does not disclose or suggest a manipulated proportion of (+) and (−) enantiomers of indacrinone, or the combination of such a manipulated proportion with amiloride or other pyrazinoylguanidine diuretics.

U.S. Pat. No. 4,087,542 discloses the diuretic (+) isomer and uricosuric (−) isomer of 6,7-dichloro-2,3-dihydro-5-(2-thienyl)benzofuran-2-carboxylic acid and manipulating the ratio of these isomers to achieve a balance of diuretic and uricosuric properties. However, manipulation of these isomers requires total separation of the diuretic and uricosuric activity between the two isomers so that the manipulation of these isomers is not suggestive of the possibility of manipulating the (+) and (−) enantiomers of indacrinone, a wholly different compound. Furthermore, there is no known currently marketed or experimental drug in which a ratio of enantiomers, other than the synthetically occurring 50:50, is used.

U.S. Pat. Nos. 4,177,285 and 4,182,764 disclose [1-oxo-2-aryl or thienyl-2-substituted-5-indanyloxy (or thio)]alkanoic acids and derivatives thereof and methods for separating the optically active isomers from racemic mixtures of these compounds by using an optically active base. There is no suggestion in these patents of manipulating the (+) and (−) enantiomers of such compounds.

Efficient, asymmetric alkylation reactions have been a goal long sought after in organic synthesis. The recent literature [S. Hashimoto, *et al.*, *Tet. Lett.*, 573–76 (1978); A. I. Meyers, *et al.*, *J. Am. Chem. Soc.*, 103, 3081–87 (1981); D. Enders, *Chemtech*, 504–13 (1981); and, K. Saigo, *et al.*, *Bull. Chem. Soc. Jap*, 52, 3119

(1979)]reports three-step sequences to achieve such a goal in high enantiomeric excesses (i.e., e.e.s) via: 1) reaction of a substrate with a chiral molecule to produce a new, modified chiral substrate molecule; 2) alkylation of the new, modified chiral substrate molecule; and, 3) subsequent reaction to liberate the desired chiral alkylated substrate and regenerate the original chiral molecule. Although high e.e.s can be achieved by these procedures, they are long, complex, and require the use of stoichiometric quantities of a chiral molecule.

Chiral phase transfer mediated alkylations offer a potentially simple, one-step solution to this problem. J. C. Fiaud [*Tet. Lett.*, 3495-96 (1975)]reports the first attempt at such using cyclic β-ketoesters as substrates and an ephedrinium bromide as a catalyst. Enantiomeric excesses (e.e.s) of 15% were claimed by Fiaud using his procedures. Enantiomeric excesses of this magnitude are considered to be insignificant from the aspect of useful chiral catalysts. Regardless, E. V. Dermlow, et al. [*J. Chem. Res.*,(S), 292-293 (1981)]later established that Fiaud's claimed e.e.s were non-existent under the conditions reported.

Indacrinone, which is a 50:50 mixture of the (+) and (−) enantiomers of [(6,7-dichloro-2,3-dihydro-2-methyl-1-oxo-2-phenyl-1H-inden-5-yl) oxy]acetic acid [hereinafter referred to and identified as indenyloxy acetic acid], is a potent, high ceiling diuretic.

The (+) and (−) enantiomers of idenyl-oxy acetic acid are represented by the formulae:

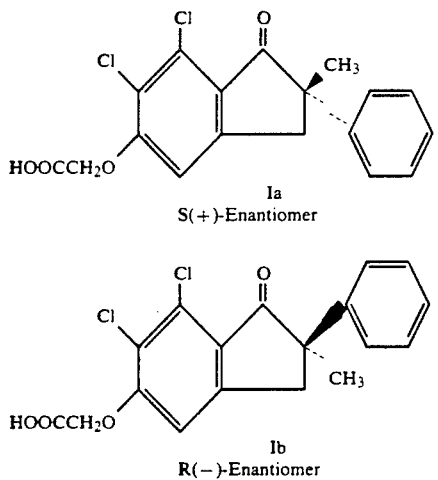

The idenyl-oxy acetic acid compound is a racemic mixture of these enantiomers, and methods for its preparation are described in U.S. Pat. No. 4,096,267. Methods for resolving the racemic mixture into its (+) and (−) enantiomers are also described in said patent, as well as in deSolms et al., *J. Med. Chem.*, Vol. 21, No. 5, pp. 437-443 (1978).

As mentioned earlier, diuretics are valuable therapeutic agents useful in the treatment of cardiovascular and renal diseases, for example in the management of all types and grades of severity of congestive heart failure and in the treatment of mild, moderate, and severe forms of hypertension. As a result of the loss of water and electrolyte, dramatic improvement is noted in peripheral and pulmonary edema, dyspnea, orthopnea, ascites and pleural effusion. Diuretics also provide effective therapy in various forms of renal edema, for example, edema associated with nephrosis and certain types of nephritis. Their administration results in prompt excretion of retained fluid and electrolytes, especially sodium chloride.

In addition to its potent diuretic and saluretic properties, this idenyl-oxy acetic acid compound also possesses important uricosuric properties as well. However, this uricosuric activity presents a complex picture, as will be apparent from the following discussion.

(1) Both enantiomers of idenyl-oxy acetic acid possess uricosuric activity. The (−) enantiomer, which is 20 to 40 times more potent than the (+) enantiomer as a natriuretic agent, possesses uricosuric activity on an acute basis; i.e., within the first few hours of administration, but on a chronic basis, produces hyperuricemia. The uricosuric activity seen on an acute basis is considered to result from the increased flow of water through the renal tubule produced by the (−) enantiomer together with somewhat decreased reabsorption of urate produced by blockade of that reabsorption by the (−) enantiomer. As the acute phase passes and administration of the (−) enantiomer becomes chronic, a decrease in the extracellular fluid volume results which produces a significantly enhanced rate of urate reabsorption. Thus, as the extracellular fluid volume becomes depleted, uricosuria ceases and urate reabsorption increases to the point that hyperuricemia results.

Both the (−) and (+) enantiomers have significant intrinsic uricosuric activity; and it seems probable that they both act on the same site or sites in the proximal portion of the renal tubule which regulate urate reabsorption. When the (−) enantiomer is administered by itself, or when a racemic mixture of (−) and (+) enantiomers is administered, the final result or net effect will be hyperuricemia, since the higher natriuretic potency of the (−) enantiomer overcomes the urate reabsorption inhibitory potency of both the (−) and (+) enantiomers through the mechanism of extracellular fluid depletion, as explained above.

(2) Both the (+) and (−) enantiomers of idenyl-oxy acetic acid possess natriuretic properties. As mentioned above, the (−) enantiomer is significantly more potent as a natriuretic agent than the (+) enantiomer. However, the (+) enantiomer does have modest potency as a natriuretic agent which, again, further complicates the problem of manipulating the proportion of (+) and (−) enantiomers in order to achieve a balance of diuretic and uricosuric properties.

(3) There is no currently known practical way of reliably associating the degree of extracellular fluid volume depletion, which leads to hyperuricemia, with the extent of urate reabsorption inhibition, which results in uricosuria.

(4) The (+) enantiomer is considered to have a different site of action in the renal tubule from that of the (−) enantiomer, with correspondingly different therapeutic effects. (These sites of action and therapeutic effects are to be distinguished from the urate reabsorption regulation which occurs in the proximal renal tubule for both enantiomers, as already explained above.) The natriuretic activity of the (−) enantiomer is considered to be effected in the ascending limb of Henle's loop portion of the renal tubule. The (+) enantiomer, on the other hand, probably expresses its therapeutic effects in a more distal portion of the renal tubule.

(5) Uricosuric activity is only desirable in the context of avoiding hyperuricemia and its consequences. Since there is no known advantage to a hypouricemic state and since extensive uricosuria occasionally causes urate precipitation in renal tubules, the goal of manipulating the proportion of (+) and (−) enantiomers is to achieve, as nearly as possible, an isouricemic or slightly hypouricemic state; that is, administration of the indacrinone final product should result in neither a rise nor a large fall in patient serum uric acid levels.

As used in this context, the term "slightly hypouricemic" means a decrease in serum or plasma uric acid levels of 20% or less from the starting level for a particular patient, or from the mean starting level for a group of patients. The starting level may be a "normal" level of uric acid or it may be a "hyperuricemic" level. It is important to avoid hypouricemia of a greater extent than that indicated, since it is thought that it can result in acute rena d by tubular urate precipitation. Thus, use of ticrynafen can cause a decrease in plasma uric acid levels of as high as 40%, which is considered undesirably high.

DESCRIPTION OF THE INVENTION

It has now been found that the process of the present invention provides a novel, simple, direct, fast and economical means for obtaining compositions possessing potent diuretic and saluretic action together with uricosuric action which achieves an isouricemic or slightly hypouricemic result in human beings through the use of a controlled range of component ratios for the enantiomers of [(6,7-dichloro-2,3-dihydro-2-methyl-1-oxo-2-phenyl-1H-inden-5-yl) oxy]acetic acid; i.e., indenyl-oxy acetic acid, via a direct chiral synthesis of intermediates to obtain the desired or required ratios.

Accordingly, the process of the present invention provides a direct chemical synthesis for obtaining a composition of matter comprising in combination, (a) the (+) enantiomer of indenyl-oxy acetic acid; and (b) the (−) enantiomer of indenyl-oxy acetic acid; wherein the weight ratio of (a):(b) can be controlled as desired or required.

The combination indacrinone enantiomer product obtained by the process of the present invention can be administered to patients in a variety of therapeutic dosages and forms in conventional vehicles as, for example, by oral administration in the form of a table or gelatin capsule, or by intravenous injection. Also, the daily dosage of the product may varied over the range of from 20:2.5 to 200:20 mg, (+):(−) once daily, preferably a daily dosage of from 45:5 to 90:10 mg. The dosage may be, for example, in the form of tablets containing 25, 50 or 100 mg of the active ingredient for the symptomatic adjustment of the dosage to the patient being treated.

A suitable unit dosage form for the combination indenyl-oxy acetic acid enantiomer product produced by the process of the present invention can be prepared by mixing 50 mg of the enantiomer combination with 75 mg of pregelatinized starch, 75 mg of microcrystalline cellulose, and 2 mg of magnesium stearate and compressing the mixture into a tablet. Similarly, by employing more of the active ingredient and less pregelatinized starch and microcrystalline cellulose, other dosage amounts can be put up in tablets. If desired, gelatin capsules and other unit dosage forms can be prepared to incorporate the combination of indenyl-oxy acetic acid enantiomers by conventional methods; or, the combined enantiomers can be made up as an injectable solution by methods well-known to pharmacists.

In general, the process of this invention is illustrated in the Reaction Scheme set forth hereinbelow and comprises preparing a racemic 2-phenylindanone VI; converting said 2-phenylindanone to a 2-methyl-2-phenylindanone enantiomer intermediate VII in the presence of a chiral catalyst under appropriate reaction conditions which intermediate contains the (+) and (−) enantiomer mixtures in pharmaceutically effective ratios as desired or required; and, demethylating, alkylating and hydrolyzing said enantiomeric mixture to obtain the optically active (+) and (−) enantiomers of idenyl-oxy acetic acid I. By choice of catalyst, methylating agent, and reaction conditions, the ratio of the 2-methyl enantiomers VII can be varied incrementally in either direction from the 1:1 mixture produced by an achiral process. Accordingly, the process of this invention enables one to directly obtain; i.e. without the need to separate intermediates, (+):(−) isomer ratios of from about 98:2 to about 2:98. Such enantiomeric excesses in alkylations are unprecedented in the literature under such simple, direct reaction conditions.

The chiral catalysts that can be employed in the process of the invention are generally referred to as N-alkyl cinchona alkaloids such as those represented by the group consisting of N-benzylcin-choninium halide, N-benzylcinchonidinium halide, N-benzylquininium halide, N-benzylquinidinium halide, their dihydro analogs, and their o-, m-, and/or p-substituted benzyl analogs wherein the substituents can be -NO$_2$, -CN, -F, -Cl, -Br, -I, -OCH$_3$, -OCH$_2$, C$_3$, -CF$_3$, -CH$_3$, and the like. Other arylalkyl analogs of such catalysts can also be employed in the process of the invention.

A group of substituted cinchona alkaloid catalysts have been established for use in the process of the present invention and it is believed that the application of these catalysts in alkylation reactions to produce unprecedented enantiomeric excesses in a fully controlled manner is novel. This group of substituted cinchona alkaloid catalysts can be represented by the general formula

wherein:
R is hydrogen, alkyl having up to 12 carbon atoms, methoxy, chlorine, fluorine, bromine, CF$_3$, nitro, cyano, and similar groups and multiples thereof;

A is benzylcinchoninium, benzylcinchonidinium; benzylquininium, benzylquinidinium; and, X is halo (i.e., F, Br, Cl, I), OH, or other simple anionic group.

The amount of catalyst that can be employed in the process of the invention can be in the range of about 0.1 to 50 mole percent, preferably 5 to 20 mole percent, per mole of the racemic 6,7-dichloro-5-methoxy-2-phenylindanone VI.

The process of the invention also requires the use of a solvent, a methylating agent, and an aqueous base in addition to the chiral catalyst.

The solvent that can be employed can be any aprotic, aromatic hydrocarbon, chlorinated hydrocarbon, or simple hydrocarbon such as toluene, benzene, ethyl benzene, propyl benzene, methylene chloride, cyclohexane, and the like. The amount of solvent employed can be in the range of about 5–100 mls, preferably 30–60 mls, per gram of the racemic 2-phenylindanone VI.

The methylating agent that can be employed in the process of the invention can be a member of the group: methyl chloride, methyl bromide, methyl iodide, dimethylsulfate, and the like, and can be employed in amounts of 1-25 molar equivalents per mol of racemic 2-phenylindanone VI. When relatively active methylating agents are used such as, for example, methyl iodide, lesser amounts of about 1-3 molar equivalents can be employed. On the other hand, when relatively inactive methylating agents are used such as, for example, methyl chloride, greater amounts of about 3-12 molar equivalents or more should be employed.

The aqueous base employed in the process of the invention is one wherein the base is an alkali metal salt selected from the group of sodium hydroxide, potassium hydroxide, lithium hydroxide, sodium carbonate, potassium carbonate, and the like. The concentration of alkali metal salt can be in the range of about 2-50% and the amount of aqueous base employed can be in the range of about 5-20 mls, preferably 8-15 mls, per gram of racemic 2-phenylindanone VI.

The process of the invention can be conducted at temperatures of from about −10° C. to about 50° C., preferably 10°-25° C., and should be accompanied with sufficient stirring of the reaction medium to ensure that thorough mixing of the solid and liquid phases is obtained and then maintained throughout the reaction process.

The process of the invention permits one to directly obtain in a single reaction step, methylated indanones in the desired (+) and (−) isomer ratios which can then be converted to the (+) and (−) enantiomers of [(6,7-dichloro-2,3-dihydro-2-methyl-1-oxo-2-phenyl-1H-inden-5-yl)]acetic acid; i.e., indenyl-oxy acetic acid, in high yields and with high optical purity. Further, the process of the invention permits one to obtain these (+) and (−) isomers at (+):(−) weight ratios as desired or required for therapeutic, pharmaceutical use.

The process of the invention is further described in the following Reaction Scheme.

Reaction Scheme

Step A

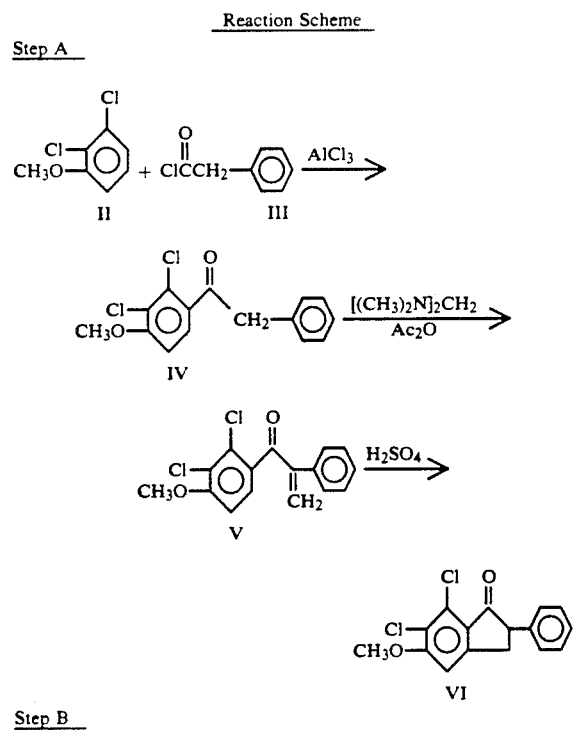

Step B

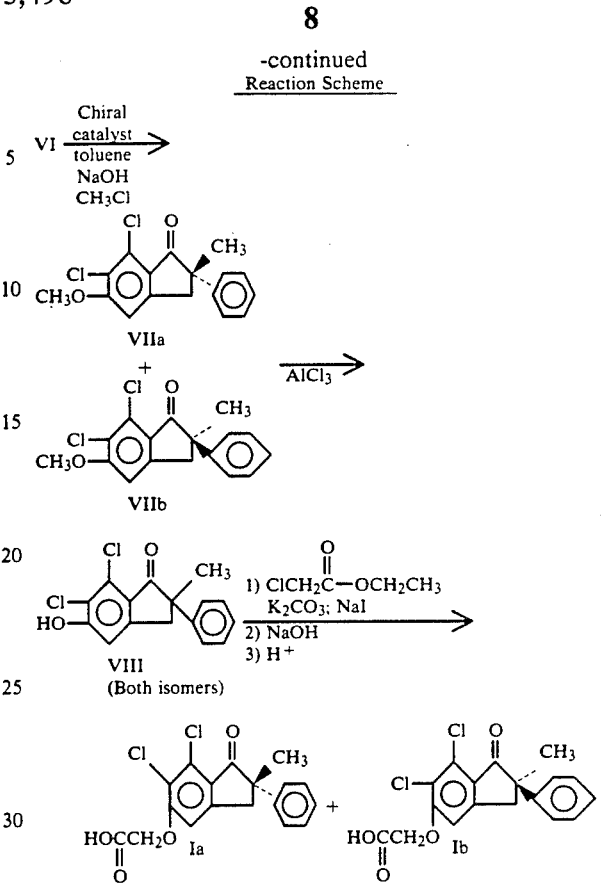

As shown in Step A of the foregoing Reaction Scheme, 2-phenylindanone VI is prepared by reacting commercially available dichloroanisole II with phenylacetyl chloride III in the presence of catalyst (AlC6 3) to produce phenylacetophenone IV which, under Mannich condensation conditions, is converted to acrylophenone compound V. Acrylophenone compound V is, in turn, cyclized by treatment with a strong mineral acid (e.g., H2SO4) to racemic 2-phenylindanone VI. This reaction is well known and has been reported by de Solms, et al., J. Med. Chem., 21, (1978), 437–443.

Racemic 2-phenylindanone VI is the starting material for the process of the invention. As shown in Step B, indanone VI is directly converted to the methylated intermediate VII containing the (+) and (−) enantiomers by treating indanone VI with methyl halide and an aqueous base (e.g., 50% aqueous sodium hydroxide) in an organic solvent (e.g., toluene) in the presence of a chiral catalyst at a temperature, of about 15° C. The 2-methylated (+) and (−) enantiomer of intermediate VII can then be O -demethylated in the presence of a catalyst (AlCl3) to obtain the optically active intermediate (+) and (−) enantiomer indanone mixture VIII which, in turn, can then be alkylated, hydrolyzed, and acidified to obtain the pure (+) and (−) enantiomers of indenyl-oxy acetic acid I at a yield of about 65-80%.

Alternatively, indanone VI can first be treated with the organic solvent and aqueous base at about 20° C. for about 5-8 hours to produce a salt of indanone VI which can then be treated with the chiral catalyst and methylating agent (halide) to obtain enantiomer indacrinone intermediate VII. This route requires less catalyst and less methylating agent while affording higher yields of the 2-methylated enantiomer intermediate VII.

The ratio of (+):(−) enantiomers in the methylated intermediate enantiomer mixture VII and the amount thereof obtained from racemic indanone VI is dependent on balancing the process conditions; e.g. methyl chloride concentration, amount of catalyst employed, temperature control, stirring, and volumes of the organic and aqueous phases. For example, if greater amounts of the (+) enantiomer are desired in the 2-methyl enantiomer intermediate VII, this can be achieved by adjusting the concentration of catalyst employed, using a less polar solvent, using a lower temperature, and decreasing the amount of methylating agent. Thus, employing about 10 mole percent of catalyst per mole of indanone VI will generally require a methyl chloride concentration of about 8–10 mols per mole of indanone VI to obtain (+) and (−) enantiomers in intermediate VIII at a (+):(−) enantiomer weight ratio of 90:10 and a yield of about 90–95%.

By employing the mirror image of the chiral catalyst and maintaining the other process parameters constant, 2-methyl enantiomer intermediate VII can be obtained at the same yield containing a (+):(−) enantiomer ratio of about 10:90 instead of 90:10. Thus, catalyst selection permits intermediate VII to be obtained containing desired ratios of (+):(−) enantiomers ranging from about 90:10 to 10:90. Subsequent O-demethylation, alkylation, and hydrolysis affords optically active (+) and (−) enantiomers of indenyl-oxy acetic acid I in desired ratios which can then be isolated by crystallization in methylene chloride or by forming a salt thereof and then isolating the thusly formed salt.

The process of the invention is further illustrated by the following examples wherein all temperatures are in °C.

EXAMPLE 1

[(6,7-Dichloro-2,3-dihydro-2-methyl-1-oxo-2-phenyl-1H-inden-5-yl) oxy]acetic acid Step A: 6,7-Dichloro-5-methoxy-2-methyl-2-phenyl-1-indanone [(+):(−) weight ratio=95:5]

A 35 ml glass pressure bottle, fitted with an efficient magnetic stirrer was charged with 25 ml of toluene. Methyl chloride (1.01 g, 20 mmole) were dissolved in the toluene and to this solution there were added 0.61 g (2 mmole) of 6,7-dichloro-5-methoxy-2-phenyl-1-indanone, 0.21 g (0.4 mole) of N-p-(trifluoromethylbenzyl) cinchoninium bromide and 5 ml of 50% aqueous sodium hydroxide. The reaction mixture was sealed with a screw cap and vigorously stirred for 18 hours at room temperature (22–25° C.). The reaction mixture was then diluted with 25 ml of toluene and 15 ml of water. The aqueous layer was separated and the toluene layer was washed twice with 25 ml of 4N hydrochloric acid. An aliquot of the toluene solution was concentrated in vacuo to dryness on a rotary evaporator. An LC assay indicated a 98% yield while an NMR assay using the chiral shift reagent [tris-[3-(heptafluoropropylhydroxymethylene)-d-camphorato ]europium (III)]showed a (+):(−) isomer ratio of 95.3:4.7.

Step B: 6,7-Dichloro-5-hydroxy-2-methyl-2-phenyl-1-indanone

The toluene solution of compound VII from Step A was dried by azeotropic distillation of water with toluene and then concentrated to approximately 20 ml. To the dry, stirred solution of the indanone, 0.7 g of aluminum chloride was added. The mixture was then warmed and stirred at 45° C. for 4 hours. The reaction was quenched at 45° C. by addition of 10 ml of water. The aqueous layer was separated at 80–85° C. and the toluene layer was washed at 80–85° C. with 10 ml of water. The solution was dried by azeotropic distillation.

Step C: [6,7-Dichloro-2,3-dihydro-2-methyl-1-oxo-2-phenyl-1H-inden-5-yl) oxy]acetic acid To the suspension of indanone compound VIII (Step B) in toluene at 20° C. to 25° C. there was added 0.5 g of potassium carbonate and 0.05 g of sodium iodide. The reaction mixture was dried by azeotropic distillation and the volume was adjusted to approximately 3 to 5 ml. The reaction was cooled to 40° C. and 0.4 g of ethyl chloroacetate was added. The reaction mixture was heated to reflux for 18 hours. The mixture was then cooled to 40° C., 4.0 ml of 2.5N sodium hydroxide was added, and the reaction was refluxed for 1 hour. Water (5 ml) was added and the internal temperature was adjusted to 80° C. The phases were allowed to separate and the bottom aqueous layer containing the product was cut. The aqueous solution was cooled to 20–25° C. and, after addition of 20 ml of toluene, was acidified with 3 ml of concentrated hydrochloric acid. The mixture was heated to reflux, the aqueous layer was allowed to separate, and the toluene layer was washed with 5 ml of water at 85° C. The solution was concentrated to 10 ml and then cooled to 20–25° C. over several hours. Cyclohexane (10 ml) was added and the mixture was stirred for 24 hours. The product was filtered, washed with toluene and dried in vacuo at 50° C., yield: 65% overall. The product was recrystallized from methylene chloride and confirmed by NMR and LC analyses.

EXAMPLE 2

Following the same procedure as Example 1 above, but using 25 ml of toluene, 0.66 g (13.1 mmole) of methylchloride 0.61 g (2 mmole) of 6,7-dichloro-5-methoxy-2-phenyl-1-indanone, 0.213 g (0.4 mmole) of N-p-trifluoromethylbenzyl cinchonidinium bromide and 5 ml 50% aqueous sodium hydroxide yielded a (+):(−) isomer ratio of 30.7:69.3. Final product was obtained following the same procedures as described in Example 1, Steps B and C.

EXAMPLE 3

A 300 ml stirred autoclave was charged with a suspension of 3.68 g (12 mmole) of 6,7-dichloro-5-methoxy-2-phenyl-1- indanone and 0.51 g (1.2 mmole) of N-benzylcinchoninium chloride in 150 ml of toluene. To the stirred mixture, 30 ml of 50% aqueous sodium hydroxide was added. The reactor was evacuated three times (25 to 29″ Hg) and flushed with nitrogen. The reaction mixture was cooled to 15° C. and the evacuated reactor was charged with 160 mmoles of methyl chloride. The reaction was stirred at 1200 rpm for 22 hours at 15° C. The reaction mixture was flushed out of the reactor with 150 ml of toluene and 60 ml of water. The aqueous layer was separated and the toluene solution was washed two times with 100 ml of 4N hydrochloric acid and once with 100 ml of water. The toluene solution was concentrated in vacuo to dryness on a rotary evaporator. An LC assay indicated a 97% yield and an NMR assay as in Example 1 above showed a (+):(−) isomer ratio of 90:10. Final product was obtained following the same procedures as described in Example 1, Steps B and C.

EXAMPLE 4

Using the procedure as described in Example 3, but employing the enantiomer of N-benzylcin-choninium chloride, a (+):(−) isomer ratio of 10:90 can be obtained. The enantiomer of cinchonine can be prepared by the procedures described by G. Grethe *et al. Helv. Chim Acta,* 56, 1485 (1973) and J. Gutzwiller and M. R. Uskokovic, ibid., 56. 1494 (1973) and references cited therein. Final product can be obtained following the procedures described in Steps B and C, Example 1.

EXAMPLE 5

Using the same procedure as described in Example 3 above, the following quantities were employed: 1.84 g (6 mmole) of 6,7-dichloro-5-methoxy-2-phenyl-l-indanone, 0.25 g (0.6 mmole) of N-benzyl-cinchoninium chloride, 75 ml of toluene, 42 mmole of methyl chloride, 15 ml of 50% aqueous sodium hydroxide and 15° C., there was obtained a 98:2 weight ratio of (+):(−) enantiomers. Final product was obtained following the same procedures as described in Example 1, Steps B and C.

EXAMPLE 6

Using the same procedure as described in Example 3 above, the following quantities were employed: 1.84 g (6 mmole) of 6,7-dichloro-5-methoxy-2-phenyl-1-indanone, 0.25 g (0.6 mmole) of N-benzyl-cinchoninium chloride, 75 ml of toluene, 5 psi of methyl chloride, 30 ml of 50% aqueous sodium hydroxide at 19° C., there was obtained an 80:20 weight ratio of (+):(−) isomers. Final product was obtained following the same procedures as described in Example 1, Steps B and C.

What is claimed is:

1. A catalyst having the formula:

A—X wherein A is benxylcinchoninium, benzylcinchonidinium, benzylquininium, benzylquinidinium or the dihydro analogs thereof, wherein A is substituted on the phenyl part of the benzyl group with $CF_3$ [or with chlorine on the 3 and 4 positions,]and the anionic species X is halo, hydroxy or other simple anion.

* * * * *